United States Patent
Rice et al.

(10) Patent No.: US 9,161,543 B2
(45) Date of Patent: Oct. 20, 2015

(54) BIOCONTROL THROUGH THE USE OF CHLORINE-STABILIZER BLENDS

(75) Inventors: Laura E. Rice, Saint Charles, IL (US); Andrew J. Cooper, Oswego, IL (US); Elisa M. Luth, Midlothian, IL (US); Wen Li Tu, Shanghai (CN)

(73) Assignee: NALCO COMPANY, Naperville, IL (US)

( * ) Notice: Subject to any disclaimer, the term of this patent is extended or adjusted under 35 U.S.C. 154(b) by 74 days.

(21) Appl. No.: 13/289,547

(22) Filed: Nov. 4, 2011

(65) Prior Publication Data

US 2013/0101682 A1 Apr. 25, 2013

(30) Foreign Application Priority Data

Oct. 21, 2011 (CN) .......................... 2011 1 0328584
Oct. 21, 2011 (CN) .......................... 2011 1 0328654

(51) Int. Cl.
| | |
|---|---|
| *A01P 1/00* | (2006.01) |
| *A01P 3/00* | (2006.01) |
| *A01N 59/00* | (2006.01) |
| *B01D 65/02* | (2006.01) |
| *C02F 1/76* | (2006.01) |
| *C02F 103/28* | (2006.01) |

(52) U.S. Cl.
CPC ................ *A01N 59/00* (2013.01); *B01D 65/02* (2013.01); *B01D 2321/168* (2013.01); *C02F 1/76* (2013.01); *C02F 2103/28* (2013.01); *C02F 2209/06* (2013.01)

(58) Field of Classification Search
CPC ....... A01N 59/00; A01N 59/23; A01N 43/80; A01N 37/34; A01N 65/00
See application file for complete search history.

(56) References Cited

U.S. PATENT DOCUMENTS

| | | |
|---|---|---|
| 3,170,883 A | 2/1965 | Owen et al. |
| 3,328,294 A | 6/1967 | Self et al. |
| 3,749,672 A | 7/1973 | Golton et al. |
| 3,767,586 A | 10/1973 | Rutkiewic et al. |
| 5,464,563 A | 11/1995 | Moore et al. |
| 5,565,109 A | 10/1996 | Sweeny |
| 5,942,240 A | 8/1999 | Merianos et al. |
| 5,976,386 A | 11/1999 | Barak |
| 6,117,817 A | 9/2000 | Lindner et al. |
| 6,132,628 A | 10/2000 | Barak |
| 6,270,722 B1 | 8/2001 | Yang et al. |
| 6,475,394 B2 | 11/2002 | Xiong et al. |
| 6,478,972 B1 | 11/2002 | Shim et al. |
| 6,533,958 B2 | 3/2003 | Shim et al. |
| 6,710,017 B2 | 3/2004 | Unhoch et al. |
| 7,067,063 B2 | 6/2006 | Barak |
| 7,311,878 B2 | 12/2007 | Singleton et al. |
| 7,550,060 B2 | 6/2009 | Jacobson et al. |
| 7,651,622 B2 | 1/2010 | Barak |
| 7,776,363 B2 * | 8/2010 | Rice et al. ..................... 424/661 |
| 2002/0003114 A1 | 1/2002 | Sweeny et al. |
| 2002/0108911 A1 | 8/2002 | Xiong et al. |
| 2003/0029612 A1 | 2/2003 | Burd et al. |
| 2003/0029812 A1 * | 2/2003 | Burns et al. ..................... 210/764 |
| 2003/0228373 A1 | 12/2003 | Ludensky et al. |
| 2006/0089285 A1 | 4/2006 | Ahmed et al. |
| 2006/0231505 A1 | 10/2006 | Mayer et al. |
| 2008/0160104 A1 | 7/2008 | Ramesh et al. |
| 2008/0199901 A1 * | 8/2008 | Enzien et al. ..................... 435/29 |
| 2010/0173018 A1 * | 7/2010 | Marais .......................... 424/713 |

FOREIGN PATENT DOCUMENTS

| | | |
|---|---|---|
| CN | 1535250 A | 10/2004 |
| EP | 0785909 B1 | 4/2003 |
| JP | 31492 | 3/1981 |
| KR | WO0142145 A1 | 6/2001 |
| KR | WO03073848 A1 | 9/2003 |
| TW | 200904990 | 2/2009 |
| TW | 201029937 A | 8/2010 |
| WO | WO2004/002896 A1 * | 1/2004 ..................... 424/665 |
| WO | WO2004026770 A1 | 4/2004 |

* cited by examiner

*Primary Examiner* — Audrea Buckley
(74) *Attorney, Agent, or Firm* — Benjamin Carlsen (57) ABSTRACT

A composition and methods of its use, the composition comprising: a halogen source, urea, and an additional halogen stabilizer excluding urea, optionally an alkali in a concentration sufficient to provide said composition with a pH of greater than 10; and optionally excluding a stabilized bromine compound from said composition is disclosed. Additionally, a method for reducing biological activity in a process stream is disclosed. The method comprises: providing a composition to a process stream, wherein said composition contains: a halogen, urea, and an additional halogen stabilizer excluding urea, optionally an alkali in a concentration sufficient to provide said composition with a pH of greater than 10; and optionally excluding a stabilized bromine compound from said composition. The invention is also directed to compositions and methods of their use as effective biocidal agents for water streams.

18 Claims, 4 Drawing Sheets

BIOCONTROL THROUGH THE USE OF CHLORINE-STABILIZER BLENDS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

At least one invention pertains to compositions and methods for reducing biological activity in process streams, e.g. water based process streams. Biological activity in process streams is problematic for a variety of reasons, including, but not limited to sanitation problems, process equipment efficiency problems, and product quality problems. For example, in papermaking processes, high biological activity levels have a deleterious effect on equipment operation. The problems associated with manufacturing certain paper types, e.g. tissue/recycled products, are more pronounced, because high fungal levels present the quandary of providing a biocide program that stabilizes the biocide well enough so that it is not readily consumed (good persistence) and providing a biocide at sufficient levels to combat periodic spikes in biological activity—a need for less stabilization/decreased persistence. Moreover, bleaching/processing of recycled fiber presents the additional quandary for papermakers because papermakers are balancing the addition of sulfite post bleaching/processing of recycled fibers, which quenches a halogen, e.g. chlorine, with the need to maintain chlorine in the system, more specifically, a persistent level of chlorine in the papermaking system without having to add more halogen/chlorine than is necessary. Thus, there is a need for a further refinement of biocide-stabilizer formulations and delivery protocols, which can treat systems more effectively and in an environmental friendly manner, such as using less chlorine/halogen, which in turn reduces halogen by-product formation.

At least one invention relates to methods and compositions effective at stabilizing oxidant biocides. Oxidant biocides such as peroxide acid and halogen chemicals like sodium hypochlorite have been widely used in the pulp and paper industry. These oxidant biocides are highly effective at immediately killing large numbers of microorganisms. Unfortunately, after their introduction into process water systems, oxidant biocides are not naturally stable and they tend to oxidize rapidly and over time lose their effectiveness. In environments with very high populations of microorganisms such as in process water which is rich in organic and inorganic material on which the microorganisms can feast, sufficient numbers of microorganisms can survive until after the oxidant biocides have lost effectiveness. As a result, unless there is sufficient residual biocide present, the microorganism population will soon recover from an oxidant biocide treatment. In some cases, halogen tolerant bacteria strains develop due to repeated introduction of single oxidant biocide. This can result in systems suffering from out of control bacterial growth. (See for example the textbook: *Disinfection, Sterilization, and Preservation*, Fifth Edition, by Seymour S. Block, Lippincott Williams & Wilkins, (2001) at least in pp. 31-57).

This problem is compounded by the fact that repeated applications of oxidant biocides is in many contexts, not commercially feasible. Many oxidant biocides cause adverse effects on paper brighteners, dyes, and other additives required to produce commercially acceptable paper products. Repeated introduction of oxidant biocides can also corrode many pieces of papermaking machinery.

One technique used to address this problem is to stabilize the oxidant biocides allowing them to suppress the viability of microorganisms over a long time while weakening the negative impact that the oxidant biocides have on the resulting paper and the papermaking equipment. As described in U.S. Pat. Nos. 3,328,294, 3,749,672, 3,170,883, 5,565,109 and 7,651,622 previous attempts at stabilizing oxidant biocides included the use of sulfamic acid, sulfamate stabilized chlorine, monochloramine, DMH stabilized halogen, AmBr—$Cl_2$, and organic nitrogen stabilized chlorine. While somewhat stable, these attempts have proven to be less effective biocides than desired. N-hydrogen sources have also been used to stabilize oxidant biocides but they too have been unsatisfactory because they are volatile and too rigid in their dosage requirements. This rigidity prevents the kind of flexible molar ratio adjustments that are often required to suit the specific conditions of the particular water system they are used to treat. Therefore there is a clear need and utility in an enhanced stabilized halogen biocide which is effective, compatible with other biocides, and flexible in dosage and concentration.

Another technique to address this problem is described in US Published Patent Applications 2006/0231505A and 200310029812A1 where they disclose the use of biocide blends. Such blends typically include an oxidant halogen which provides an initial large kill of the organisms and another longer lasting but less effective biocide which provides more long term microorganism suppression. Unfortunately many biocides are themselves incompatible with other biocides and the use of multiple biocides, each having their own preparation and introduction issues, requires an inordinate investment in complex application equipment. Furthermore, multiple biocide feeding machines be installed at various points along a papermaking production line thereby vastly increase the cost and complexity of adding the biocides. So there remains need for simplified making biocide and feeding approach.

The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed to a composition comprising: a halogen source, urea, and an additional halogen stabilizer excluding urea, optionally an alkali in a concentration sufficient to provide said composition with a pH of greater than 10. Optionally the composition excludes a stabilized bromine compound. The stabilizer may comprise one item from the list consisting of: an N-hydrogen compound, ammonia, ammonium salts, ammonium sulfamate, ammonium sulfate, sulfamic acid, sodium sulfamate, cyanuric acid, succinimide, urea, glycouril, glycine, amino acids, and any combination thereof. The stabilizer may comprise at least two compositions of matter each of which function as a halogen stabilizer. The halogen source may be selected from the group consisting of at least one of the following: a chlorine source, an alkaline hypohalite, $Cl_2$ gas, NaOCl, Ca(OCl)$_2$, and electrically generated chlorine. The composition may contain: an alkaline hypohalite, urea, and ammonium sulfamate. The urea and additional halogen stabilizer may be in a ratio of 50:50 with one another.

At least one embodiment of the invention is directed to a method for reducing biological activity in a process stream comprising providing the composition to a process stream. The composition may be added to the process stream by the following mode of addition: forming a mixture of at least an alkali in a concentration sufficient to maintain a pH of greater than 10 in the final composition and an alkaline hypohalite, and secondarily mixing said mixture with a second mixture containing urea and said additional stabilizer, wherein said secondary mixing is optionally done with a T-mixer. The process stream may be a papermaking process stream. The papermaking process may be a process selected from the group consisting of: tissue and/or towel, board; packaging; pulping; and recycled pulping. The process stream may contain fungus. The process stream may have a sulfite concentration of between 2 ppm to 50 ppm. The method may further comprise monitoring the biological activity in the process stream prior to and subsequent to the addition of said composition. The biological activity may be monitored by taking a sample of said process stream and plating said sample on a Petri dish or similar apparatus or by measuring ATP levels of a sample from the process stream or by taking a sample of said process stream and monitoring dissolved oxygen and optionally the oxidation reduction potential of said sample and optionally responding by adding or reducing the amount of one or more chemistries which are added to said process stream, wherein said chemistries include said composition. The method may further comprise adding a second composition to said process stream that contains a halogen, urea, and excludes an additional N-hydrogen compound.

At least one embodiment of the invention is directed to a method of preventing the growth of microorganisms in a process water stream. The method includes the step of: introducing a composition into the process water stream. The composition comprises: a halogen source, a halogen stabilizer containing a mixture of a sulfur bearing species with urea and/or ammonium sulfate at any ratio, and optionally an alkali. The sulfur bearing species includes sulfamic acid or its salt equivalent. The molar ratio of sulfamic acid to halogen atoms in the halogen source is more than 2:1.

The sulfur bearing species may further comprises a nitrogen stabilizer. The nitrogen stabilizer may be one item selected from the group consisting of ammonium sulfate, sodium sulfamate, and any combination thereof. The molar ratio of halogen to all of the sulfur in the sulfur bearing species may be more than 2:1. The alkali may be sodium hydroxide. The halogen may be chlorine, sodium hypochlorite, 1,3,5-Trichloroisocyanuric acid (TCCA), 1-bromo-3-chloro-5,5-dimethyl-2,4-imidazolidedione (BCDMH) and 1,3-dichloro-5,5-dimethyl-2,4-imidazolidedione (DCDMH). The method may further comprise the steps of first adding to the sulfamic acid an alkali and then the adding urea and/or sodium sulfate.

The process water stream may be so rich in food for microorgasnisms that a single halogen oxidant biocide is not effective at exterminating the microorganisms population but the composition is. The process water stream may be one selected from the list consisting of a cooling tower water stream, and papermaking process water stream. The ratio of sulfamic acid or its salt to nitrogen stabilizer may be optimized at any ratio between the concerns of biocidal efficacy and impact on chemical additive present in the process water stream. The ratio of sulfamic acid or its salt to nitrogen stabilizer may be optimized at any ratio between the concerns of biocidal efficacy and corrosion on equipment present in the process water stream. The composition when used in a papermaking process might not reduce the effectiveness of OBA and DYE additives on paper made from that process. The salt may be sodium sulfamate.

Additional features and advantages are described herein, and will be apparent from, the following Detailed Description.

BRIEF DESCRIPTION OF THE DRAWINGS

A detailed description of the invention is hereafter described with specific reference being made to the drawings in which.

DETAILED DESCRIPTION OF THE INVENTION

The following definitions are provided to determine how terms used in this application, and in particular how the claims, are to be construed. The organization of the definitions is for convenience only and is not intended to limit any of the definitions to any particular category.

"Alkali" means a composition of matter that functions as a pH altering chemical base.

"DYE" or "Dye" means one or more compositions used in the papermaking industry to alter the optical properties of a substrate. Dyes often contain chromophoric groups and auxochrome and have good affinity to fiber and compatibility to other additive in paper industry.

"Nitrogen stabilizer" means a stabilizer which contains at least one nitrogen atom.

"OBA" means a dye or pigment based optical brightening agent which is a component of a coating formulation commonly applied to a paper substrate. Dyes or pigments that absorb ultraviolet radiation and reemit it at a higher frequency in the visible spectrum (blue), thereby effecting a white, bright appearance.

"Pigment" means a solid material used in a papermaking process to alter the optical properties of a substrate.

"Halogen Source" means a halogen atom by itself or a halogen atom associated with a cationic counterpart.

"Halogen Stabilizer" means a halogen based material whose presence in proximity to a composition of matter functioning as an oxidizing biocide increases the amount of time that the composition remains in a sufficient chemical state to continue functioning as a biocide, this includes but is not limited to materials which preserve (or slow down the rate of loss of) the oxidizing capability of the biocide composition.

"Stabilizer" means a composition of matter that increases the length of time that oxidizing halogen ions retain oxidant capacity and are capable of releasing free ions slowly thereby remaining an effective biocidal agent in a liquid environment.

"Substrate" means a sheet of paper, a sheet of paper precursor, a mass of fibers, or any other cellulose based or synthetic fibrous material that can be coverted into a sheet of paper by a papermaking process.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

As stated above, the present invention provides for a composition and a method of use for said composition, which reduces biological activity in a process stream by providing a more efficient application of a biocide. In turn the biocide is more efficiently utilized, e.g. increase in persistence of the biocide in the system when needed, which can provide an environmental benefit because a process operator can use less biocide to combat various types of microorganisms and bacteria that pervade process streams, e.g. including water based systems, wherein one water based system example is a papermaking system.

The composition contains at least the following components: halogen, urea, and an additional halogen stabilizer excluding urea. Stabilizers can be blended with chlorine or bromine to yield a milder oxidant. Benefits of halogen-stabilization include increased persistence of the halogen residual for improved control of microbial growth in biofilm or surface deposits and in systems with long residence times and high halogen demand.

Halogen-stabilization can also improve compatibility of the halogen with sensitive process additives, including dyes, optical brightening agents, polymers, and corrosion control products. However, it has been observed in several instances that the halogen becomes too persistent when it is blended with stabilizers, for example urea. As a result, the program may not adequately control fungi and several types of bacteria, including sphingomonads and spore-forming bacteria. Some forms of stabilized-halogen are more volatile, reducing the halogen residual available in the water-phase and contributing to vapor-phase corrosion.

In at least one embodiment optionally, there is an additional component: an alkali in a concentration sufficient to provide a pH of greater than 10. In at least one embodiment, the pH is greater than 12. In yet a further embodiment, the pH range is from 12 to about 13.5. An alkali can include one or more of the following chemistries: sodium hydroxide and potassium hydroxide.

Optionally, there is an additional component: excluding a stabilized bromine compound from said composition.

With respect to the halogen, in at least one embodiment, the halogen is selected from at least one of the following: a chlorine source, alkaline hypohalite, $Cl_2$ gas (e.g. added to $H_2O$ stream prior to blending), NaOCl, $Ca(OCl)_2$, and electrically generated chlorine.

In at least one embodiment the composition comprises urea in combination with additional stabilizer, including ammonium Sulfamate, to stabilize halogens for biocontrol In at least one embodiment, the stabilizer is an N-hydrogen compound.

In at least one embodiment, the N-hydrogen compound is ammonium sulfamate.

In at least one embodiment, the N-hydrogen compound excludes ammonium sulfate.

In at least one embodiment, the composition contains: an alkaline hypohalite, urea, and ammonium sulfamate.

The ratios between urea and an additional stabilizer can vary depending upon system conditions, e.g. levels of fungus. For example, one could take into account chemical kinetics between: (a) urea with halogen; (b) additional stabilizer with halogen; and (c) blend of urea and additional stabilizer with halogen.

In at least one embodiment, the stabilizer blend between urea and the additional stabilizer is 50:50.

A method for reducing biological activity in a process stream is also disclosed, e.g. process stream contained in a water system. The method comprises: providing a composition to a process stream, wherein said composition contains: a halogen, urea, and an additional stabilizer excluding urea, optionally an alkali in a concentration sufficient to provide said composition with a pH of greater than 10; and optionally excluding a stabilized bromine compound from said composition.

In at least one embodiment, the composition is added to the process stream by the following mode of addition: forming a mixture of at least an alkali in a concentration sufficient to provide a pH of greater than 10 and an alkaline hypohalite, and secondarily mixing said mixture with a second mixture containing urea and said additional stabilizer, wherein said secondary mixing is optionally done with a T-mixer.

In at least one embodiment, the method comprises: adding a second composition to said process stream that contains a halogen, urea, and excludes an additional N-hydrogen compound.

With respect to the order of addition of the components, In at least one embodiment, the composition is added to the process stream by the following mode of addition: forming a mixture of at least an alkali in a concentration sufficient to provide a pH of greater than 10, preferably 12 to 13.5, and an alkaline hypohalite, and secondarily mixing said mixture with a second mixture containing urea and an additional stabilizer. One of ordinary skill in the art could mix the first mixture and second mixture via a variety of techniques, e.g. apparatuses.

In at least one embodiment, the first mixture and second mixture are mixed together with a T-mixer. One of ordinary skill the art would understand what a T-mixer is.

In at least one embodiment, one of ordinary skill in the art can utilize a mixing chamber, such as the one disclosed in U.S. Pat. No. 7,550,060, herein incorporated by reference, to carry out a mixing protocol of the chemistries.

The methodology of the present invention is applicable to a variety of process streams or aqueous based systems or water based systems or industrial based systems or a combination thereof.

In at least one embodiment, the process stream is a papermaking process stream.

In at least one embodiment, the papermaking process is a process selected from the group consisting of: tissue and/or towel, board; packaging; pulping; and recycled pulping.

In at least one embodiment, the process stream contains fungus.

In at least one embodiment, the process stream has a sulfite concentration of between 2 ppm to 50 ppm.

The efficacy of the composition for reducing biological activity can be measured by a variety of analytical techniques and controls schemes.

In at least one embodiment, the process stream further comprises monitoring said biological activity in said process stream prior to and subsequent to the addition of said composition.

In at least one embodiment, the biological activity is monitored by taking a sample of said process stream and plating said sample on a Petri dish or similar apparatus.

In at least one embodiment, the biological activity is monitored by measuring ATP (adenosine triphosphate) levels of a sample from said process stream.

In at least one embodiment, the biological activity is monitored by taking a sample of said process stream and monitoring dissolved oxygen and optionally the oxidation reduction potential of said sample and optionally responding to said biological activity by adding or reducing the amount of one or more chemistries which are added to said process stream, wherein said chemistries include said composition.

The compositions by themselves or compositions utilized to treat a process stream can be made outside of the process stream or within the process stream (in situ) or a combination thereof.

In at least one embodiment a composition comprising a halogen, a halogen stabilizer, and optionally an alkali are provided for inhibiting the growth of microorganisms in a papermaking environment. The stabilizer is a composition comprising sulfur. The sulfur bearing species includes sulfamic acid (or its salt equivalent such as sodium sulfamate). The molar ratio of the halogen to the sulfamic acid is more than 2:1. By having such a large ratio of halogen to stabilizer, it has been observed that an unexpected biocidal effect occurs. This was quite surprising as at a molar ratio of 1:1 of halogen to sulfamic acid, no significant anti-biological efficacy was observed. Moreover because the stabilizers are needed to stabilize the halogens, it would be expected that more stabilizer relative to halogen would better stabilize the halogen, yet the opposite is the case.

In at least one embodiment the stabilizer is a composition comprising a mixture of sulfur bearing species with urea. The halogen is mixed with sulfamic acid at molar ratio of Nitrogen to Chlorine of more than 2:1. By having such a stabilizer mixture of stabilized halogen, it has been observed that an unexpected synergistic effect occurs which results in the halogen remaining stabilized for a longer period of time, and without impairing the quality of the produced paper or corroding the papermaking equipment.

In at least one embodiment the stabilizer is a composition comprising a mixture of sulfur bearing species with ammonium sulfate.

In at least one embodiment the sulfur bearing species further comprises a nitrogen stabilizer.

In at least one embodiment the nitrogen stabilizer is one item selected from the group consisting of ammonium sulfate, sodium sulfamate, or any combination thereof.

In at least one embodiment the molar ratio of halogen to all of the sulfur in the sulfur bearing species is more than 2:1.

In at least one embodiment the alkali is sodium hydroxide.

In at least one embodiment the halogen are chlorine, sodium hypochlorite, 1,3,5-Trichloroisocyanuric acid (TCCA), 1-bromo-3-chloro-5,5-dimethyl-2,4-imidazolidedione (BCDMH) and 1,3-dichloro-5,5-dimethyl-2,4-imidazolidedione (DCDMH).

In at least one embodiment the sulfamic acid is first amended with alkali and then the urea/ammonium sulfate is added. Sodium hypochlorite is added to above mixture.

In at least one embodiment the sulfur baring nitrogen combined sodium hypochlorite first at molar ratio more than 2:1 nitrogen to chlorine and then is added to urea or ammonium sulfate.

In at least one embodiment the urea or ammonium sulfate combined sodium hypochlorite first then is added to sulfur baring nitrogen at different ratio. The order is significant because different stabilized halogen species are generated at different rates due to differing equilibrium constants. These differences can be accounted for by dosing the halogens in different amounts and in different orders. Also chlorine is able to transfer from stabilized chlorine to other nitrogen species so the order of combinations can compensate for that.

In at least one embodiment the composition contains no buffer.

In at least one embodiment the composition contains no alkali.

In at least one embodiment the composition can be formulated on site by mixing the components together before mixing with halogen oxidant.

Figure 1:
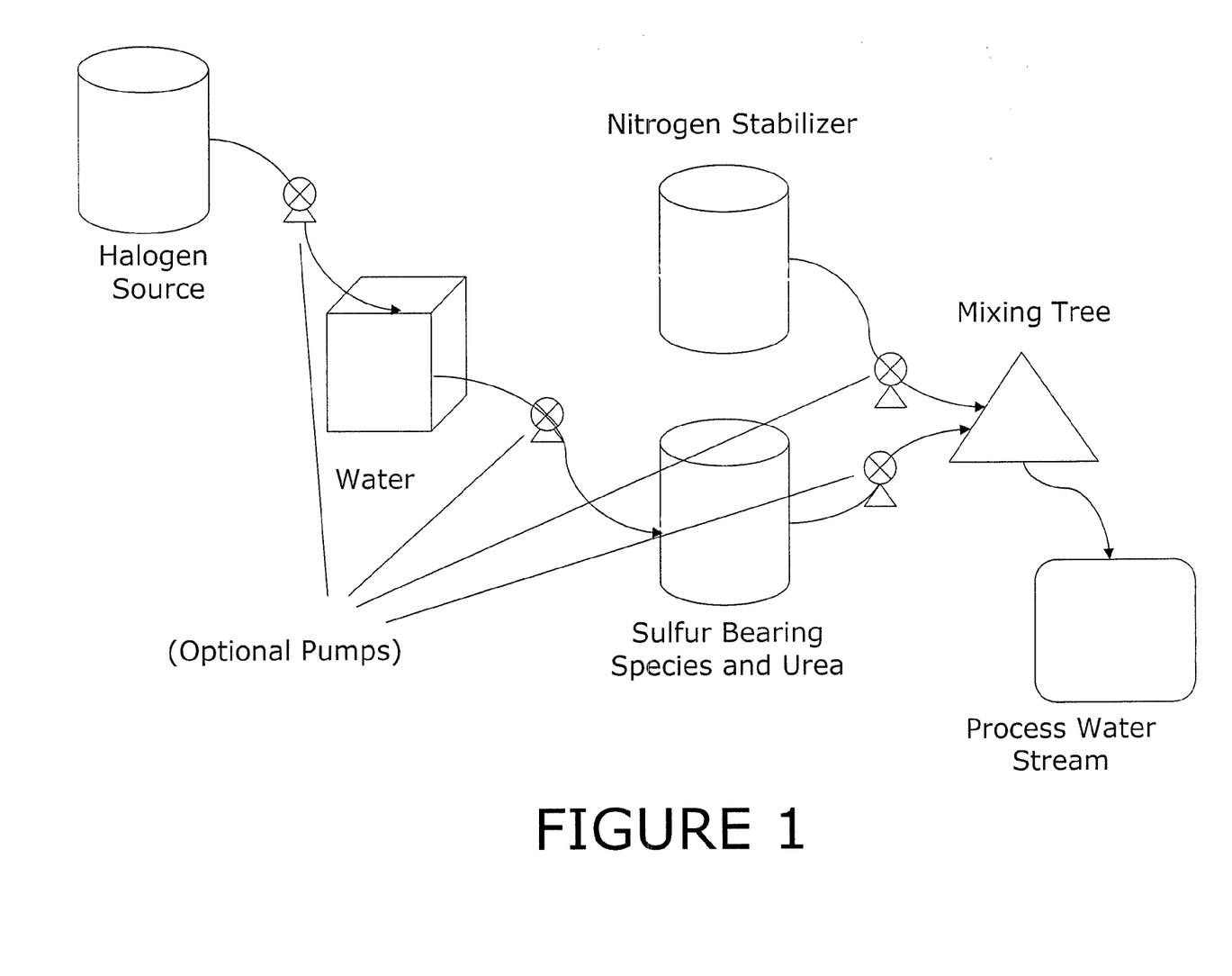
FIG. 1 is a flowchart illustrating one method of combining constituents of the biocide composition.
Figure 2:
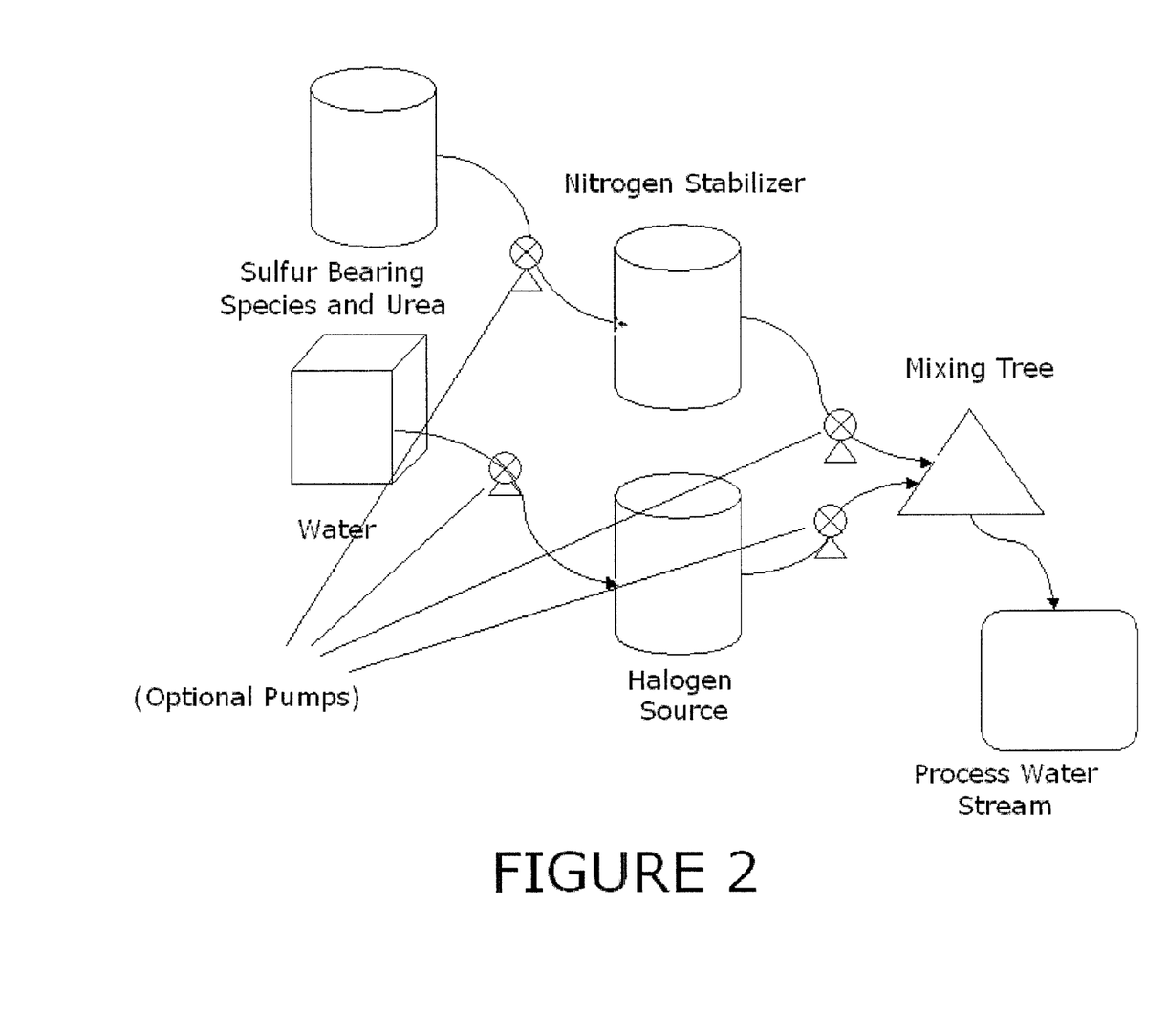
FIG. 2 is a second flowchart illustrating one method of combining constituents of the biocide composition.
Figure 3:
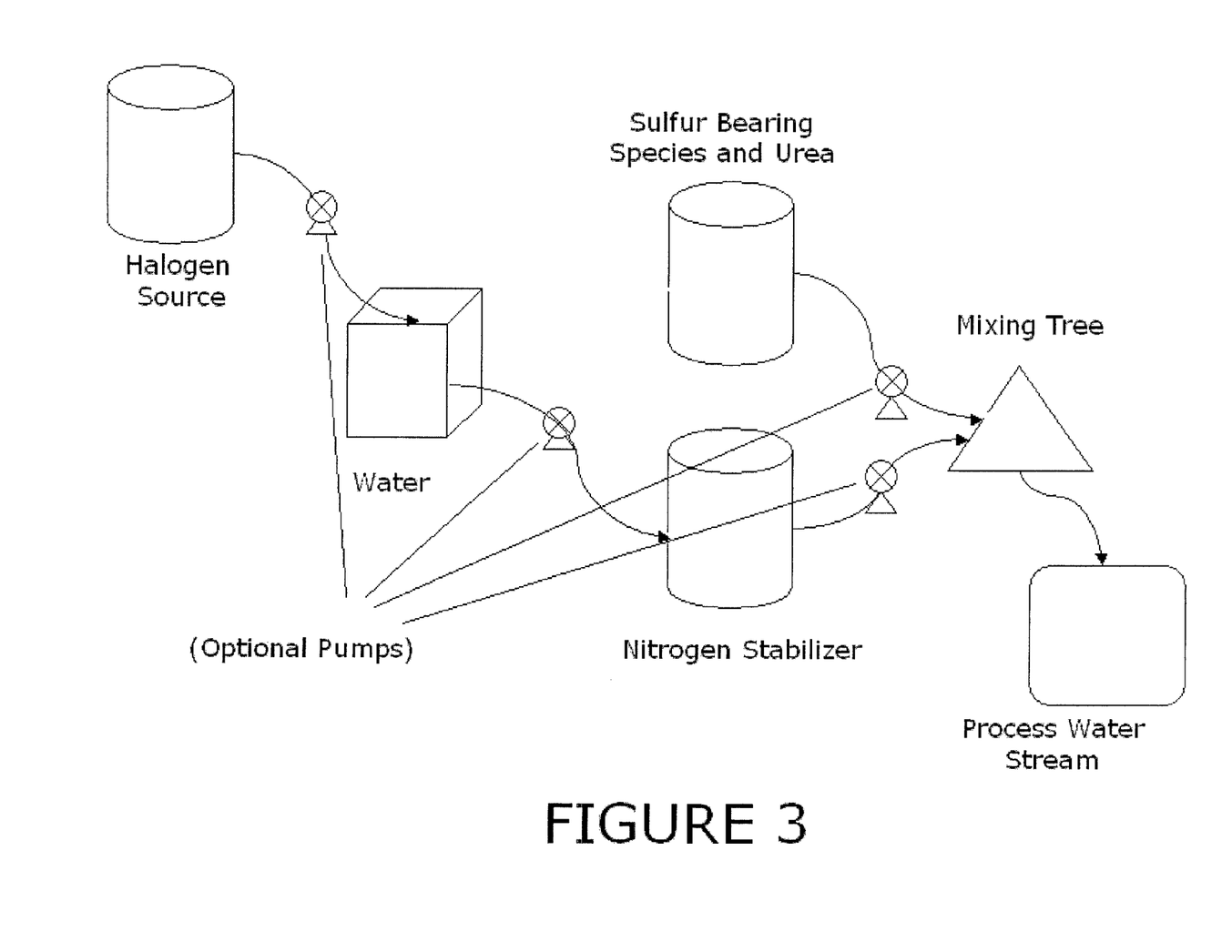
FIG. 3 is a third flowchart illustrating one method of combining constituents of the biocide composition.

In at least one embodiment the composition can be formulated on site by mixing the components as illustrated in any one of FIGS. 1, 2, and/or 3.

In at least one embodiment the microorganisms killed by the biocide are sessile. In at least one embodiment the microorganisms killed by the biocide are planktonic.

One noted benefit of the invention is the fact that the sulfamic acid and the nitrogen stabilizer readily combine so when mixing the two a high product yield is achieved with little waste. In addition, unlike stand alone stabilizers containing inorganic nitrogen stabilizers, the mixture of sulfamic acid and nitrogen stabilizer functions at many different ratio amounts. As a result the relative amounts of sulfamic acid or nitrogen stabilizer can be appropriately increased or decreased depending on the particular environment it is to be used in. For example in cases where nitrogen stabilizer may interfere with particular paper additives such as OBA or DYE, the relative amount of sulfamic acid will be increased. In contrasts in contexts where the sulfamic acid has compatibility issues, the amount of nitrogen stabilizer can be increased.

In at least one embodiment the details of the formulation is targeted towards the nature of the biological infestation. For example if bacteria are just beginning to infiltrate one or more items of process equipment, a formulation containing relatively equal amounts of sulfamic acid and the nitrogen stabilizer is used because it is optimized to causes low impact on additives and low degrees of corrosion which is more desirable than a highly effective biocide when the infestation is weak. In contrast, when the contamination is intense or long term colonization, effectiveness of the biocide is more important than the one time effects on additives or corrosion and a therefore a formulation containing more sulfamic acid relative to the molar amount of nitrogen stabilizer is used. Thus by using a formulation having only two variables, a number of condition specific ratios can be provided which requires a simple input system yet is capable of dynamically responding to different conditions over the life cycle of the industrial facility.

In at least one embodiment the composition is used as a biocidal agent in a cooling tower.

In at least one embodiment the composition is used to reduce biofilm on a surface. Biofilm is the accumulation of sessile organisms on the surfaces of equipment. Such accumulations often pose particular problems as the available exposed surface area for the biocide to work on is reduced. Moreover there is often a tradeoff between biocide efficacy and impact the biocide has on biofilms yet the invention avoids harmful effects on process equipment yet effectively neutralizes biofilms.

In at least one embodiment the composition is used to treat microorganisms in a membrane system. Membrane systems are often prone to biofilm colonization as microorganisms find their surfaces (because of composition, shape, or both) attractive. As they are also very delicate relative to other forms of process equipment, the general tradeoff issues are even more pronounced in membranes. Fortunately the composition is effective at treating membrane biofilms without damaging them. In at least one embodiment the membrane system is a water permeable membrane. In at least one embodiment the membrane is a part of a water treatment system.

In at least one embodiment the composition has a particular pH before it is introduced into the system. In at least one embodiment the pH is greater than 5 and less than 12, and is most preferably between 8 and 10.

In at least one embodiment the ratio of the contents of the composition are balanced to optimize the composition's effectiveness and utility. In the prior art chlorosulfamate was used in a ratio of 1:1 with chlorine. This resulted in stronger than desired bonding of the chlorine and as a result it reduced the rate of releasing sulfamate from sulfate thereby reducing the effectiveness of the composition. In at least one embodiment the ratio is different and as a result the composition is more effective. In at least one embodiment the ratio of sulfamate to stabilizer within the composition is between (less than 4):1 and (more than 1):1. Experimental data has shown that in some circumstances ratios of 1:1 and 4:1 do not work at all or at best work poorly, ratios of 8:1 to 4:1 work somewhat and that 3:1 is highly effective as a biocide. This demonstrates that an unexpected sysnergistic effect based on more than just concentration is at work which is wholly novel and unexpected.

EXAMPLES

The foregoing may be better understood by reference to the following examples, which are presented for purposes of illustration and are not intended to limit the scope of the invention.

A number of biocide formulations were prepared and were applied to samples of process water from a paper mill. Their compositions and effectiveness are listed in FIG. 4 and in Table 1. Table 1 illustrates that a composition comprising 12% Sulfamic Acid and 3% Ammonium Sulfate is able to achieve high product yield without addition of NaOH. It also demonstrates that the addition of NaOH in bleach can improve feasibility of blending stabilizers at different rates.

TABLE 1

Optimization of blending condition for mixing stabilizer and sodium hypochlorite

| Stabilizer formula | Molar Ratio $Cl_2:N_2$ | TRO*** ppm | FRO**** ppm | TRO Yield % | FRO/TRO % |
|---|---|---|---|---|---|
| Caustic in Bleach = 0.5% | | | | | |
| 3% SA* + 12% AS** | 1:1 | 2200 | 61 | 29.32 | 2.77 |
| | 4:1 | 1550 | 520 | 19.26 | 33.55 |
| 7.5% SA + 7.5% AS | 1:1 | 3575 | 220 | 47.26 | 6.15 |
| | 4:1 | 3400 | 960 | 42.17 | 28.24 |
| 12% SA + 3% AS | 1:1 | 6200 | 370 | 81.31 | 5.97 |
| | 4:1 | 5400 | 2030 | 66.78 | 37.59 |
| sulfamic acid | 4:1 | 6550 | 1219 | 80.93 | 18.61 |
| Caustic in Bleach = 3.2% | | | | | |
| 3% SA + 12% AS | 1:1 | 5265 | 810 | 70.16 | 15.38 |
| | 4:1 | 4905 | 1675 | 60.95 | 34.15 |
| 7.5% SA + 7.5% AS | 1:1 | 4050 | 146 | 53.54 | 3.60 |
| | 4:1 | 8019 | 1000 | 99.45 | 12.47 |
| 12% SA + 3% AS | 1:1 | 3524 | 240 | 46.22 | 6.81 |
| | 4:1 | 6885 | 3000 | 85.14 | 43.57 |
| sulfamic acid | 4:1 | 6300 | 1450 | 77.84 | 23.02 |

Figure 4:
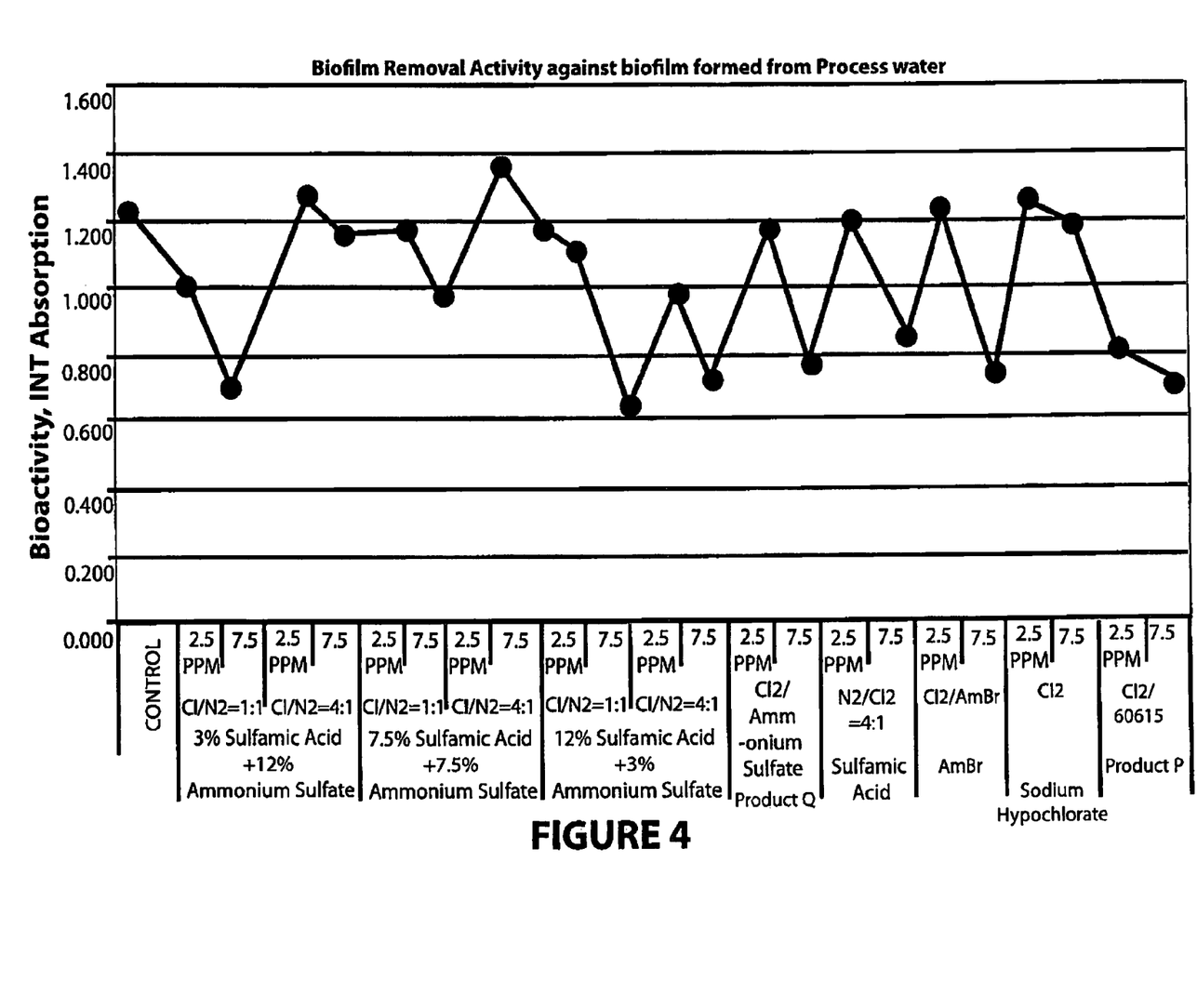
FIG. 4 is a graph displaying data which demonstrates the effectiveness of the invention.

*SA sulfamic Acid
**AS: ammonium sulfate
***TRO: total residual oxidant
****FRO: free residual oxidat FIG. 4 illustrates that 12% Sulfamic Acid and 3% ammonium sulfate showed more active on bioactivity inhibition than other combinations of stabilizers.

Without being limited in theory and the scope afforded in construing the claims, it is believed that naturally the chlorine transfers back and forth from one chloronitrogen species to another chloronitorgen species according to the equilibrium equations below and the invention makes use of the different equilibrium constants to optimize the presence of the desired reactions that produce the particularly desired chloronitrogen species that is effective as a biocide.

$H_2NSO_3H+NaOCl \Leftrightarrow ClHNSO_3H+NaOH$

$ClHNSO_3H+NaOCl \Leftrightarrow Cl_2NSO_3H+NaOH$ $(NH_4)_2SO_4+2NaOCl \Leftrightarrow 2NH_2Cl+Na_2SO_4+2H_2O$ $NH_2Cl+NaOCl \Leftrightarrow NHCl_2+NaOH$ $H_2NSO_3H+NH_2Cl \Leftrightarrow CHNSO_3H+NH_3$ $ClHNSO_3H+NH_2Cl \Leftrightarrow Cl_2NSO_3H+NH_3$ In at least one embodiment the dosing sequence of the composition is calibrated to make optimal use of the relative equilibrium rates of the various chemical reactions. Each of the chemical reactions occurs at different rates and as a result Cl species are constantly passing back and forth between molecules and have different availabilities at different times. In at least one embodiment the reagents required for the lower occurring reactions are added to the composition first and are allowed to react somewhat or completely before the reagents required for the faster reactions are added. This avoids the faster reactions competing with the slower reactions. In at least one embodiment the reagents required to allow the chlorosulfamate species to react with the amine to form chloramine and ammonia is only added to the composition after chloroamine has been partially or completely formed.

In at least one embodiment the composition is diluted to produce a more mild (and less violent, reactive, or destructive) biocide effect. In at least one embodiment the methods of diluting biocides disclosed in U.S. Pat. Nos. 6,132,628 and 7,067,063 are employed. In at least one embodiment the composition is diluted so the species exists within the range of 100 ppm to 150,000 ppm.

While this invention may be embodied in many different forms, there are shown in the drawings and described in detail herein specific preferred embodiments of the invention. The present disclosure is an exemplification of the background and principles of the invention and is not intended to limit the invention to the particular embodiments illustrated. All patents, patent applications, scientific papers, books, and any other referenced materials mentioned anywhere herein, are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for reducing biological activity in a process stream comprising:
   introducing into a process stream containing optical brightening agents a stabilized halogen, the stabilized halogen being stabilized only by urea, the stabilized halogen initially reducing the biological activity of organisms within the process stream,
   subsequently the introduced halogen reacts with the stabilizer resulting in the proliferation of sphingomonads in the process water,
   after said proliferation adding a composition into the process stream the composition comprising: a halogen source, urea, and at least one sulfur bearing species, the at least one sulfur bearing species comprising sulfamic acid, the ratio of halogen to sulfur in the at least one sulfur bearing species being more than 2:1, the at least one sulfur bearing species excludes urea, the alkali in a concentration sufficient to provide said composition with a pH of greater than 10; the halogen source comprises electrically generated chlorine, wherein the composition controls the sphingomonads but does not impair the activity of the optical brightening agents.

2. The method of claim 1, wherein said composition is added to the process stream by the following mode of addition: forming a mixture of at least an alkali in a concentration sufficient to provide or to maintain a pH of greater than 10 in the final composition and an alkaline hypohalite, and secondarily mixing said mixture with a second mixture containing urea and said additional stabilizer, wherein said secondary mixing is optionally done with a T-mixer.

3. The method of claim 2, wherein said process stream is a papermaking process stream.

4. The method of claim 3, wherein said papermaking process is process selected from the group consisting of: tissue and/or towel, board; packaging; pulping; and recycled pulping.

5. The method of claim 3, wherein said process stream contains fungus.

6. The method of claim 3, wherein said process stream has a sulfite concentration of between 2 ppm to 50 ppm.

7. The method of claim 3, further comprising monitoring said biological activity in said process stream prior to and subsequent to the addition of said composition.

8. The method of claim 7, wherein said biological activity is monitored by taking a sample of said process stream and plating said sample on a Petri dish or similar apparatus.

9. The method of claim 7, wherein said biological activity is monitored by measuring ATP levels of a sample from said process stream.

10. The method of claim 7, wherein said biological activity is monitored by taking a sample of said process stream and monitoring dissolved oxygen and optionally the oxidation reduction potential of said sample and optionally responding by adding or reducing the amount of one or more chemistries which are added to said process stream, wherein said chemistries include said composition.

11. The method of claim 3, further comprising: adding a second composition to said process stream that contains a halogen, urea, and excludes an additional N-hydrogen compound.

12. The method of claim 1 wherein the stabilizer further comprises one item from the list consisting of: ammonia, ammonium salts, ammonium sulfamate, ammonium sulfate, sulfamic acid, sodium sulfamate, cyanuric acid, succinimide, urea, glycouril, glycine, amino acids, and any combination thereof.

13. The method of claim 1 wherein the stabilizer comprises at least two compositions of matter each of which function as a halogen stabilizer.

14. The method of claim 1, wherein said halogen source further comprises one item selected from the group consisting of: a chlorine source, an alkaline hypohalite, $Cl_2$ gas, NaOCl, $Ca(OCl)_2$, and any combination thereof.

15. The method of claim 1, wherein said composition contains:
   an alkaline hypohalite, urea, and ammonium sulfamate.

16. The method of claim 1, wherein said urea and said additional halogen stabilizer are in a ratio of 50:50 with one another.

17. A method for reducing biological activity in a papermaking process stream comprising:
   introducing into a papermaking process stream a stabilized halogen, the stabilized halogen being stabilized only by urea, the stabilized halogen initially reducing the biological activity of organisms within the process stream,
   subsequently the introduced halogen reacts with the stabilizer resulting in the proliferation of sphingomonads in the process water,
   after said proliferation adding a composition into the process stream the composition comprising: a halogen source, urea, and at least one sulfur bearing species, the at least one sulfur bearing species comprising sulfamic acid, the ratio of halogen to sulfur in the at least one sulfur bearing species being more than 2:1, the least one sulfur bearing species excludes urea, the alkali in a concentration sufficient to provide said composition with a pH of greater than 10; the halogen source comprises electrically generated chlorine wherein the composition controls the sphingomonads.

18. A method for reducing biological activity in a process stream comprising:
   introducing into a process stream a stabilized halogen, the stabilized halogen being stabilized only by urea, the stabilized halogen initially reducing the biological activity of organisms within the process stream, subsequently the introduced halogen reacts with the stabilizer resulting in the proliferation of sphingomonads in the process water, after said proliferation adding a composition into the process stream the composition comprising: a halogen source, urea, and at least one sulfur bearing species, the at least one sulfur bearing species comprising sulfamic acid, the ratio of halogen to sulfur in the at least one sulfur bearing species being more than 2:1, the least one sulfur bearing species excludes urea, the alkali in a concentration sufficient to provide said composition with a pH of greater than 10; the halogen source comprises electrically generated chlorine wherein the composition controls the sphingomonads.

* * * * *